(12) United States Patent
Schmidt et al.

(10) Patent No.: US 8,597,568 B2
(45) Date of Patent: Dec. 3, 2013

(54) METHOD FOR DEACTIVATING UNDESIRED CONTAMINATIONS IN LEECH EXTRACTS

(75) Inventors: Sebastian Schmidt, Haan (DE); Jörg Peters, Haan (DE); Juergen Michels, Köln (DE)

(73) Assignee: Bayer Pharma AG (DE)

( * ) Notice: Subject to any disclaimer, the term of this patent is extended or adjusted under 35 U.S.C. 154(b) by 0 days.

(21) Appl. No.: 13/498,474

(22) PCT Filed: Oct. 8, 2010

(86) PCT No.: PCT/EP2010/065109
§ 371 (c)(1),
(2), (4) Date: Apr. 17, 2012

(87) PCT Pub. No.: WO2011/045243
PCT Pub. Date: Apr. 21, 2011

(65) Prior Publication Data
US 2012/0195791 A1    Aug. 2, 2012

(30) Foreign Application Priority Data

Oct. 13, 2009   (EP) .................................... 09172861

(51) Int. Cl.
*A61L 2/08* (2006.01)
(52) U.S. Cl.
USPC ........ 422/22; 422/24; 250/455.11; 250/432 R
(58) Field of Classification Search
USPC ............... 422/28, 22, 24; 250/455.11, 432 R; 210/748.01
See application file for complete search history.

(56) References Cited

U.S. PATENT DOCUMENTS

2007/0003430 A1* 1/2007 Kaiser et al. .................... 422/24

FOREIGN PATENT DOCUMENTS

| BE | 415 573 A | 5/1936 |
| EP | 1 676 818 A1 | 7/2006 |
| WO | WO 02/38191 A2 | 5/2002 |
| WO | WO 02/38502 A1 | 5/2002 |

* cited by examiner

Primary Examiner — Sean E Conley
(74) Attorney, Agent, or Firm — Bayer Healthcare LLC

(57) ABSTRACT

The present invention provides a method for inactivating viruses and/or bacteria in medicinal-leech extracts by means of electromagnetic radiation.

13 Claims, 7 Drawing Sheets

METHOD FOR DEACTIVATING UNDESIRED CONTAMINATIONS IN LEECH EXTRACTS

Figure 1:
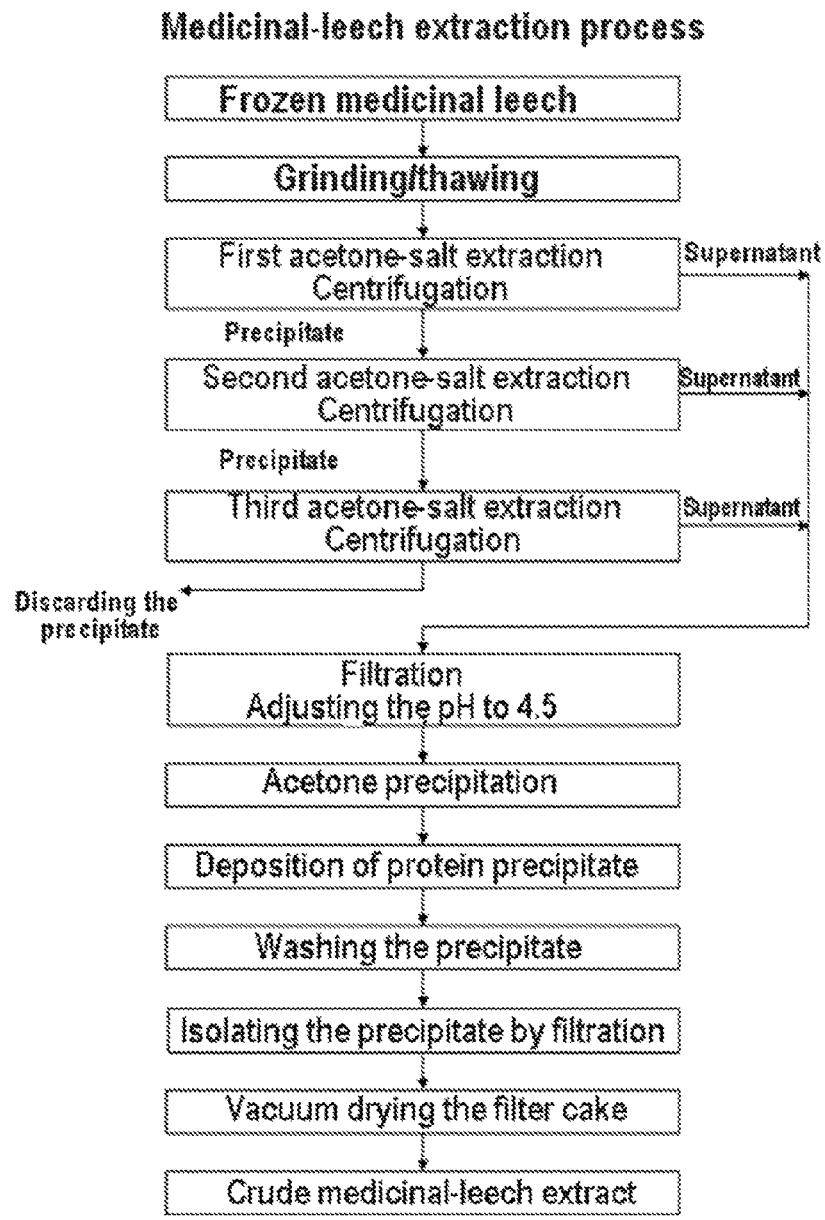

The invention is in the field of inactivation of viruses and/or bacteria by means of electromagnetic radiation. The present invention relates to a method for inactivating viruses and/or bacteria in medicinal-leech extracts.

Medicinal leeches have been used since ancient times for medical therapy. As early as in Ancient Greece and especially in the Middle Ages, use has been made of their large blood uptake capacity for the medical removal of blood from the body (bloodletting).

At the beginning of the 19th century, coagulation-inhibiting medicinal-leech extracts came onto the market. In 1955, a polypeptide called hirudin was extracted for the first time from medicinal leeches. Hirudin binds to the fibrinogen binding site of thrombin and inhibits, via an extension, the active site, blocking the action thereof.

A historical overview of medicinal-leech extracts and hirudin is given by the following publication: Nowak, G. & Schrör, K. (2007): *Hirudin—the long and stony way from an anticoagulant peptide in the saliva of medicinal leech to a recombinant drug and beyond. A historical piece*; in: Thromb. Haemost. vol. 98, pages 116-119.

To obtain therapeutically active medicinal-leech substances, frozen medicinal leeches (e.g. *Hirudo medicinalis, Hirudo verbana* and species related thereto) or constituents thereof are mechanically comminuted and homogenized. In a multi-stage extraction and purification method, it is possible to obtain an active substance which, for example, can be used in an ointment for the treatment of venous insufficiency and acute haemorrhoidal complaints.

Since medicinal-leech extracts are a product from a natural source of raw material, safety with regard to unwanted contamination such as bacteria or viruses is of great importance. When implementing a viral safety plan, the use of complementary technologies, i.e. complementary in the mechanism of action, is explicitly stipulated (see, for example, Guideline Q5A of the *International Conference on Harmonisation of Technical Requirements for Registration of Pharmaceuticals for Human Use (ICH)*). This is to ensure that a broad spectrum of viruses is covered.

Established methods for inactivating bacteria and large coated viruses are acidic treatment, treatment with organic solvents, treatment with detergents and pasteurization, which methods are carried out alone or, preferably, in combination.

However, for small uncoated viruses such as parvoviruses, for example, these methods are not effective.

One method for depleting small uncoated viruses is nanofiltration. Here, removal is achieved by size exclusion: a membrane securely retains viruses whose size is within the specified retention rate.

However, a problem in nanofiltration is that small uncoated viruses may be similar in size to the desired therapeutic substance. As a result, it is therefore not possible to safely filter out the pathogens without filtering out the protein as well. The consequence is increased, inacceptable product loss, resulting in a method which is no longer economical.

In the case of nanofiltration of medicinal-leech extracts, it became apparent in some studies that the attainable flow rate per area of membrane is extremely low. At the same time, blockage of the filter surfaces occurred even after a very short processing time. Said blockages were not reversible. It was not possible to bring the filters back to a functional state by conventional measures such as, for example, backwashing. This extremely poor performance of nanofiltration combined with high costs of filter units rules out nanofiltration methods for virus depletion of medicinal-leech extracts as an economic application in pharmaceutical manufacturing.

A further method for virus inactivation is irradiation with ultraviolet light (UV irradiation). In this method, a particular challenge is the homogeneous irradiation of the medium to be processed. The goal is reliable and extensive destruction of microorganisms and/or viruses combined with extensive preservation of the sensitive valuable substance. Especially products from natural sources of raw material have a complex, varied composition. Generally, the various product constituents exhibit differences in stability to UV irradiation. This makes it difficult to find a compromise between virus inactivation and preservation of product quality.

An important criterion for product protection is shortening product exposure in the irradiation area. Since the average treatment duration required is determined by the particles which pass the irradiation area the quickest, reduction of the treatment duration requires a very uniform residence-time distribution within the product stream. Problems when using reactors for radiating ultraviolet light into fluid media arise because radiation intensity in the medium to be treated decreases exponentially with increasing distance from the radiation source. Microorganisms and viruses at a greater distance from the radiation source are, for this reason, destroyed more slowly or no longer destroyed at all.

This effect, which is considerably intensified with increasing light-absorbing capacity of the medium, leads to the use of very large irradiation surfaces, as are found in thin-film reactors for example, in the prior art. However, the thin-film reactors used can be converted to an industrial scale only with great difficulty, since keeping the film thickness constant on a large scale can be realized only by diameter enlargement proportional to the throughput, and on an industrial scale this leads to large reactors which are no longer manageable.

A further negative effect results from the unfavourable residence-time behaviour of the liquid films, which are inevitably very thin in accordance with the mostly only low penetration depth of UV radiation into the reaction medium and which thus exhibit laminar flow, and in which any exchange transverse to the main flow direction does not take place. Because of the velocity profile which decreases linearly down to zero towards the wall, the layers close to the wall reside substantially longer than the layers further away from the wall. In order for it to be possible for the minimum irradiation dose necessary for destruction to be also realized in the liquid layer which is distant from the wall and flowing more quickly, it is necessary to raise the average residence time of the film. However, this leads to increased radiation exposure and thus to greater damage to the products.

The literature (EP 1 339 643A1, EP 1 337 280A1) describes the particularly favourable residence-time behaviour in spiral flow channels. A product flows through a helically formed flow channel. The helical flow guidance leads to secondary flows in the channel, known as Dean vortices, which guarantee intensive and, at the same time, gentle mixing. The high mixing effect of the vortices realizes a narrow residence-time distribution and dose distribution. It is thus possible to specifically introduce an effective radiation dose which is sufficient to inactivate viruses without greatly affecting the product. This so-called dose concept is independent of the module size, and so scale-up from laboratory scale to manufacturing scale is possible.

UV irradiation in a so-called spiral module is, in principle, provided in such a way that a one-time flow-through is carried out through the spiral module. Depending on the turbidity of the liquid to be processed, the flow rate in the spiral module can be varied within certain limits. The limits are determined by the required formation of secondary flow and the pressure drop in the module. If even the lowest possible flow rate and thus the longest residence time should not be sufficient to achieve the desired virus inactivation, it would be conceivable in principle to operate multiple modules in series.

However, in this case, the appropriate number is limited by the pressure drop over the arrangement of multiple modules in series and by the pressure stability of the modules.

In the case of medicinal-leech extracts, the absorbance of the liquid is so high (optical density at 254 nm is greater than 50) that the penetration depth of UV radiation in a medicinal-leech extract is limited to the region on the surface and a few micrometers therebelow. Significant virus inactivation upon passage through a single spiral module combined with maintenance of product integrity cannot be ensured. This has been shown by studies of the applicant. The potential option of operating multiple modules connected one after another was also ruled out for practical reasons. For sufficient inactivation, over 4 modules in series would have been necessary. This would not have been realizable in practice because of the associated pressure drop coupled with the limited pressure resistance of the system.

In addition, owing to the complex active-substance mixtures in medicinal-leech extracts, there is in particular the risk of film formation in the irradiation area, which formation may attenuate or even completely prevent the introduction of radiation into the medium to be irradiated.

Thus, it has to be feared that UV irradiation of medicinal-leech extracts is not an effective method for virus inactivation. Another problem is that film formation is only recognizable with great difficulty if the medium to be irradiated has a very high optical density. In such a case, it is not possible to introduce a photosensor into the medium to be irradiated and to measure the radiation intensity in order to determine film formation. There is the risk that the medium to be irradiated is insufficiently irradiated and, thus, that sufficient product safety is not ensured.

Proceeding from the prior art, the object is thus to provide a method for inactivating viruses and/or bacteria, more particularly small uncoated viruses, in medicinal-leech extracts. The desired method shall result in a higher product yield than with classic methods such as acidic treatment, solvent treatment, detergent treatment, pasteurization and/or nanofiltration and, at the same time, ensure economical operation and high product quality. In addition, the desired method shall make it possible to recognize film formation so that sufficient product safety can be ensured.

It was found that, surprisingly, virus and bacteria inactivation in medicinal-leech extracts can be achieved effectively and economically by circulating the medicinal-leech extract between a stirred vessel and an irradiation device in which the medicinal-leech extract is irradiated with ultraviolet light.

The present invention therefore provides a method for inactivating viruses and/or bacteria in a fluid medicinal-leech extract, characterized in that the extract is circulated between a stirred vessel and an irradiation device in which the extract is exposed to electromagnetic radiation.

The fluid medicinal-leech extract is preferably the extract obtained by means of the method mentioned in example 1.

Inactivation is understood to mean a process which results in the reduction or elimination of undesired properties of viruses and/or bacteria. The inactivation is carried out by introduction of electromagnetic radiation. Preferably, such irradiation is carried out with ultraviolet light, which is known to be suitable for altering viruses and/or bacteria in such a way that they no longer have a damaging effect on humans, animals, plants and/or the environment.

Ultraviolet light is understood to mean electromagnetic radiation in the wavelength range of 100 nm to 400 nm. For virus inactivation, use is preferably made of so-called UVC radiation in the range of 100 nm to 280 nm, particularly preferably in the range of 200 nm to 280 nm.

According to the invention, the medicinal-leech extract is circulated between a stirred vessel and an irradiation device. The irradiation device consists of one or more preferably parallel-connected spiral modules, which are described in detail further below.

Surprisingly, the circulatory mode of operation achieves sufficient inactivation of viruses and bacteria in medicinal-leech extracts without any damage to the proteins contained in the medicinal-leech extract. The broadened residence-time distribution caused by the use of a stirred reactor (compared to the one-time passage through one or more spiral modules connected one after another) and the increased irradiation time in the single module as a result of the circulatory mode of operation have, surprisingly, no damaging effect on the proteins contained in the medicinal-leech extract. In addition, despite the correspondingly long processing time in the single spiral module, there is surprisingly no relevant film or aggregate formation.

It was found that, surprisingly, the method according to the invention makes it possible, by irradiation with ultraviolet light, to inactivate viruses and bacteria even in medicinal-leech extracts having an optical density greater than 70. Preferably, use is made of medicinal-leech extracts having an optical density in the range of 10 to 72, particularly preferably in the range of 30 to 65, very particularly preferably in the range of 40 to 60.

Optical density OD (also known as absorbance) is understood to mean the decadic logarithm of the ratio of the intensity $I_0$ of the radiation entering a medium to the intensity I of the radiation exiting the medium:

$$OD = lg(I_0/I)$$

Optical density is dependent on the wavelength of the radiation used. In the present document, optical density at a wavelength of 254 nm is specified.

According to the invention, the medicinal-leech extract is circulated. The ratio of pump-circulated volumetric flow rate to total volume is in the range of 0.5 to 80 l/h, preferably in the range of 1 to 60 l/h, particularly preferably in the range of 3 to 45 l/h.

While carrying out the method according to the invention, the temperature of the extract is maintained at a temperature in the range of 2° C. to 25° C., preferably in the range of 4° C. to 20° C., particularly preferably in the range of 8° C. to 15° C.

In a preferred embodiment, before and/or after a batch has been irradiated in a circulatory mode of operation, a transparent medium is circulated one or more times and the intensity of the radiation introduced into the transparent medium in the irradiation area or passed through the transparent medium is measured.

This is because the optical density of a medicinal-leech extract is too high for it to be possible to measure, during irradiation of the extract, the radiation intensity entering the medicinal-leech extract in the irradiation area or even passing through the medicinal-leech extract. However, there is the risk that, over the course of irradiation, film formation occurs on the inside wall of an irradiation module. The consequence of film formation would be a reduction in the radiation intensity entering the extract. As a result, complete inactivation of viruses and/or bacteria would no longer be ensured. Therefore, a transparent medium is conveyed through the system before and/or after medicinal-leech extract irradiation and the intensity of the radiation introduced into the medium or passed through the medium is measured. If the radiation intensity before and after medicinal-leech extract irradiation is the same or approximately the same, film formation can be ruled out and the next batch of medicinal-leech extract can be irradiated. If a significant decrease in radiation intensity is recorded, it is conceivable that a film has formed on the inside wall of an irradiation module, which film should be removed before the next batch. Alternatively, it is also conceivable for the radiation intensity to be increased and/or the number of circulations to be increased, in order to compensate accordingly for the reduced radiation intensity.

A transparent medium is understood to mean a medium which has an optical density of less than 10 for a wavelength range of the radiation used (preferably measured at 254 nm).

Preferably, the transparent medium used is water or an aqueous buffer solution. Suitable buffer solutions are, for example, a phosphate-buffered saline (PBS) or other organic/inorganic buffer systems.

In addition to film formation, it is also necessary to avoid radiation-induced aggregate formation in the liquid, both with regard to the product and with regard to secondary components or both. Despite the circulatory mode of operation of the medicinal-leech extract, it was surprising that no aggregate formation at all was observed in the embodiment according to the invention.

The method according to the invention is carried out in a device comprising at least one stirred vessel, one irradiation device and one conveyor for the medicinal-leech extract.

A stirred vessel is understood to mean a container in which the medicinal-leech extract can be stored, and which comprises means for mixing the medicinal-leech extract located in the container. Typically, the means used for mixing are stirrers such as, for example, a blade stirrer. The container can, for example, consist of glass, stainless steel or a plastic.

The conveyor is used to convey the fluid medium from the stirred vessel, through the irradiation device, and back into the stirred vessel. A suitable conveyor is, for example, a pump.

The device for carrying out the method according to the invention is characterized in that the stirred vessel, the irradiation device and the conveyor are connected to one another in such a way that the medicinal-leech extract can be guided from the stirred vessel, through the irradiation device, and back again into the stirred vessel.

The irradiation device comprises one or more preferably parallel-connected spiral modules.

A spiral module is understood to mean a device providing at least one source of electromagnetic radiation and a channel winding helically around an axis. Examples of such spiral modules are shown in FIG. 5, 6, 7, 8, 9 or 10 in laid-open document WO 2002/038502A1. The helically wound channel is preferably arranged in such a way that it passes around a source of electromagnetic radiation. It is conceivable for further sources of electromagnetic radiation to be arranged around the channel.

If a fluid medium flows through such a helically wound channel, the effect on the medium is intensive, uniform cross-mixing prevailing over the entire length of the channel, which mixing is perpendicular to the main direction of product flow. Despite the laminar flow characteristics prevailing in the method according to the invention, the cross-mixing brings about a narrowed residence-time distribution. In addition, the cross-mixing ensures that the fluid layers distant from the radiation source, which layers receive little or no electromagnetic radiation particularly in the case of strongly absorbing media, undergo an intense exchange with the irradiated layers close to the radiation source. This and the narrow residence-time distribution results in all the fluid elements experiencing a uniform and even duration and intensity of irradiation, which duration and intensity can be adapted to particular needs by means of the flow velocity and the intensity of the radiation source. Thus, it is possible to ensure an effective reduction of microorganisms and/or viruses in the medium. In the case of media in which excessive irradiation can lead to damage, the risk of an unfavourably broad residence-time distribution resulting in excessive radiation exposure and thus damage in some cases is effectively prevented.

It is conceivable, in a spiral module, for multiple channels to be arranged adjacently and to be wound helically around a common axis. A channel may have an angular, circular, oval or semicircular cross-sectional profile. Further cross-sectional profiles are conceivable. Preferably, the channel has a cross-sectional profile which is flattened on at least one side. From this flattened side, electromagnetic radiation is preferably introduced into the channel. Examples of such channels are shown in FIG. 5, 6, 7, 8, 9 or 10 in WO 2002/038502A1. The cross-sectional profile of the channel is preferably D-shaped (i.e. semicircular or semielliptic), rhombus-shaped or rectangular.

A suitable source of electromagnetic radiation is any source which emits radiation at a wavelength suitable for inactivating viruses and/or bacteria. Preferably, use is made of a source of UVC radiation such as, for example, a mercury-vapour lamp which has a radiation maximum at a wavelength of 254 nm. It is conceivable to use multiple sources of electromagnetic radiation.

In a particularly preferred embodiment, the spiral module comprises a hollow cylinder onto which spiral tubing is mounted in a force-fitted or form-fitted manner. A source of electromagnetic radiation is introduced into the hollow cylinder without direct product contact. Such spiral modules are, by way of example, described in applications WO 02/38502A1, WO 02/38191A1, WO 07/096057A1, EP 1 464 342A1 and DE 10 2009 009 108.4.

WO 07/096057A2 describes, for example, a spiral module which is characterized in that spiral tubing is mounted in a form-fitted manner over an inner support tube. This produces, between the support tube and the spiral tubing, a channel which winds helically from one end of the spiral tubing, around the support tube, to the other end of the spiral tubing. Preferably, the spiral tubing is mounted in a force-fitted manner onto a hollow cylinder, as described in application DE 10 2009 009 108.4. Cross-flows between adjacent channel coils can thus be effectively avoided. Such cross-flows would otherwise result in unwanted broadening of the residence-time distribution.

The spiral modules are preferably designed such that at least the irradiated components are used as disposable parts.

The volume ratio between the stirred vessel and the irradiation device having one or more spiral modules is in the range of 1 to 1000, preferably in the range of 5 to 500, particularly preferably in the range of 10 to 200. As a result, it is possible to observe a processing time which can be easily embedded into the operational process, i.e. into a shift for example.

The device for carrying out the method according to the invention is preferably equipped with one or more sensors, for example for the irradiation (e.g. UV sensor), the pressure, the container liquid level, the temperature and the volumetric flow rate. In addition, the device is preferably equipped with sensors which monitor the correct installation position of the spiral modules, and with leakage sensors which detect potential leaks. In a preferred embodiment, safety features are also envisaged. These may, for example, be: measures to prevent unwanted irradiation of operating personnel (e.g. an enclosure with door monitoring), collection troughs in case of leakage, protection against moving machine parts.

The entire device is preferably controlled and regulated by a process control system. In particular, the temperature, the flow rate, the irradiation and the processing time are monitored.

The constituents of the device are preferably designed to be CIP-compatible (CIP=clean in place) to ensure sterilization for pharmaceutical applications.

The invention will be explained in detail below with reference to examples, without being limited thereto.

The following are shown:

FIG. 1: Diagram showing a method for obtaining a crude medicinal-leech extract

Figure 2:
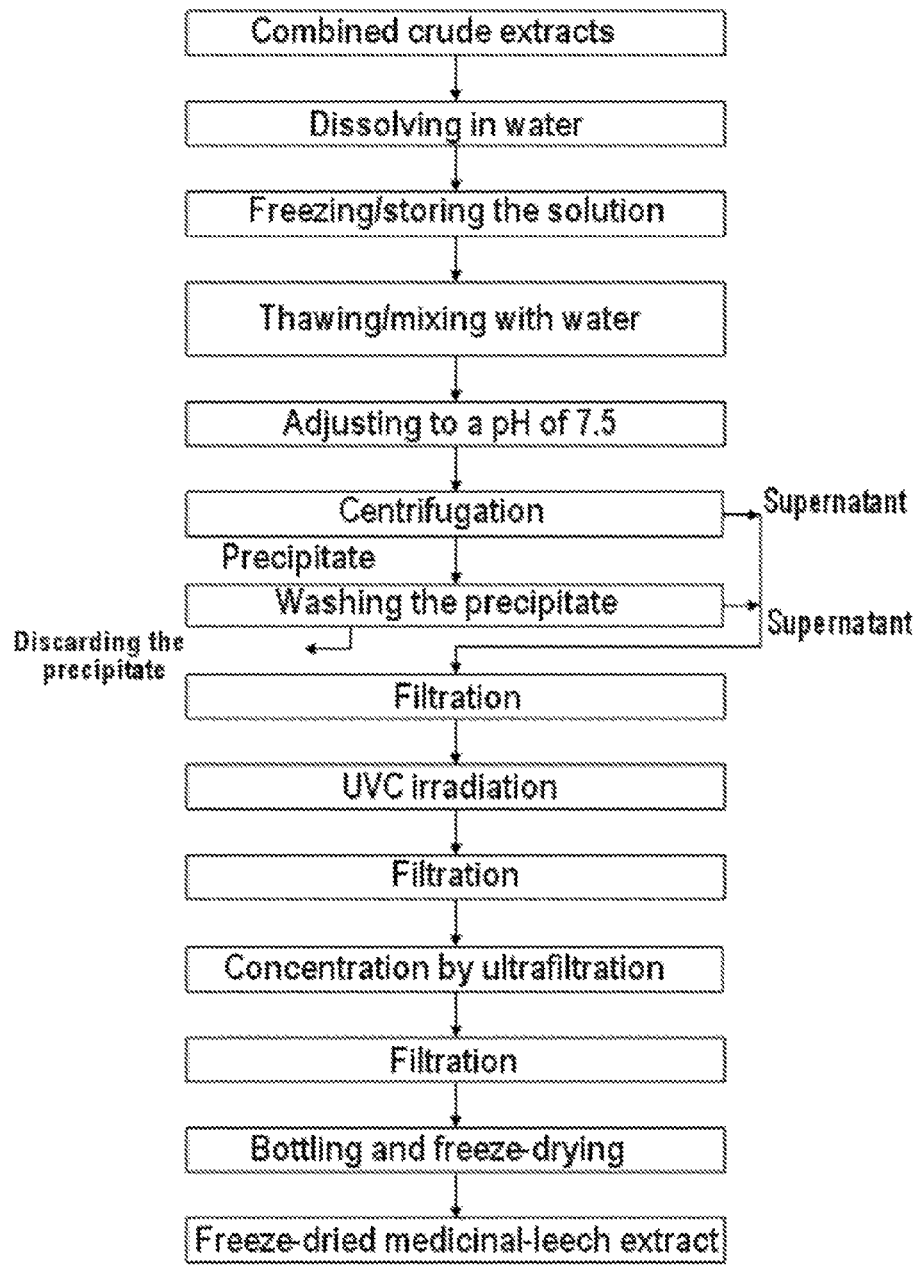

FIG. 2: Diagram showing a method for obtaining a freeze-dried medicinal-leech extract FIG. 3: Diagram showing one embodiment of a device for carrying out the method according to the invention FIG. 4: Diagram showing an irradiation module FIG. 5: Diagram showing an irradiation-module head FIG. 6: Diagram showing a helical channel through which flow occurs and in which Dean vortices form FIG. 7: Graph showing the inactivation of hirudin and viruses in a medium as a function of irradiation dose.

EXAMPLE 1

Method for Obtaining a Medicinal-Leech Extract

Method Part 1 (Obtaining Crude Extract)

Method part 1 for obtaining a medicinal-leech extract, obtaining the crude extract, is shown diagrammatically in FIG. 1.

Deep-frozen medicinal leeches were thawed and, in two portions of altogether 70-80 kg, were comminuted in a cutter. After comminution, the suspension was diluted with heated purified water and transferred to the extraction vessel, in which the volume was adjusted by addition of purified water. Sodium chloride and acetone were added to the first extraction stage while the suspension was stirred and heated further. After the first extraction stage, the suspension was separated by centrifugation into a biomass-containing phase and a liquid phase. The liquid phase was put into temporary storage. The solid phase was gathered in heated purified water and extracted again with an increased sodium chloride and acetone concentration (second extraction stage). Thereafter, centrifugation was carried out again and, finally, the third extraction step was carried out at an increased sodium chloride and acetone concentration. The biomass-containing solid phase was subsequently discarded. The liquid phases were combined, filtered, and adjusted to a pH of 4-5, preferably 4.5 (±0.1), by addition of trichloroacetic acid (TCA) before proteins were precipitated in acetone which had been stored in a freezer. The protein precipitate formed a deposit and was subsequently separated from the upper acetone phase. The precipitate was washed three times with an acetone-water mixture (80% v/v). The precipitate formed a deposit between the wash steps. The upper acetone phase was subsequently removed in each case. The washed precipitate was recovered by filtration and washed with acetone. Subsequently, the excess acetone was flushed out with nitrogen gas and the filter cake was collected. The moist filter cakes can optionally be put into temporary deep-frozen storage. The filter cakes were dried in a vacuum drying cabinet to remove residual acetone. The dried filter cakes, which contain the crude medicinal-leech extract, were put into temporary deep-frozen storage until further processing.

Method Part 2 (Obtaining Medicinal-Leech Extract (Lyophilized))

FIG. 2 shows a diagram of method part 2 for obtaining a medicinal-leech extract, obtaining the freeze-dried medicinal-leech extract.

Various dried filter cakes containing the crude medicinal-leech extract were combined and dissolved in purified water. The resulting protein solution was frozen and put into temporary storage in a freezer. Thereafter, the solution was thawed and purified water was added. The diluted protein solution was heated up and pasteurized for a defined period of time at a constant temperature. Subsequently, the protein solution was cooled to room temperature and adjusted to a neutral pH of 7-8, preferably 7.5 (±0.1), using dilute hydrochloric acid or sodium carbonate. The pH-adjusted solution was centrifuged and the supernatant was combined and put into temporary cool storage. The precipitate remaining was washed by addition of purified water and renewed centrifugation.

The supernatants were subsequently combined, homogenized and filtered. If necessary, the optical density OD (254 nm) can be appropriately adjusted by addition of purified water. Optical densities up to 72 have been found to be suitable. Subsequently, UV irradiation was carried out at a wavelength of 254 nm and at a suitable dose. Doses from 50 to 1000 $J/m^2$, preferably 100-600 $J/m^2$, particularly preferably 250-350 $J/m^2$, have been found to be suitable. The UV-irradiated protein solution was subsequently filtered and concentrated (ultrafiltration) in order to adjust the activity. The adjusted bulk solution was lastly filtered once more, filled into bottles and then freeze-dried. The freeze-dried medicinal-leech extract was put into temporary storage until further processing.

EXAMPLE 2

Device for Inactivating Undesired Contamination in a Fluid Medium Having a High Optical Density of More than 50

Figure 3:
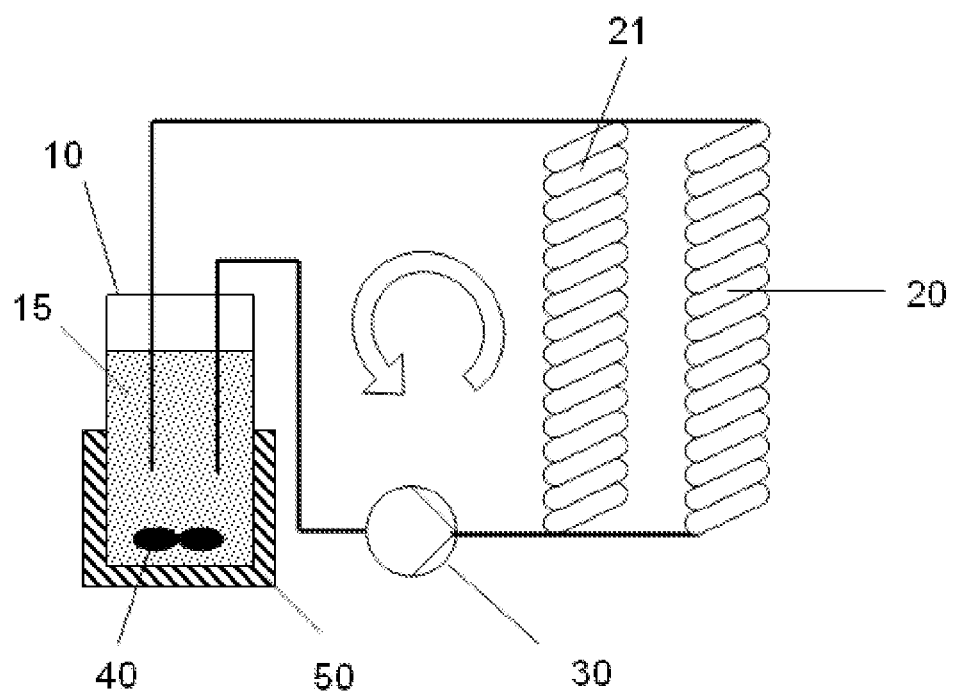

A diagram of the device for carrying out the method according to the invention is shown in FIG. 3.

The device essentially consists of a container 10, for example a stirred vessel having a stirrer 40 and one or more irradiation modules (20, 21). The medium 15 is, via tubing or tube connections, guided from the container 10, through the irradiation modules 20, 21, and then back to the container 10 again. This is preferably effected by a pump 30. The irradiation modules can be connected in parallel or in series or else combined in series and in parallel.

The irradiation module is preferably a spiral module according to the definition given above, comprising a spiral irradiation space which is guided around a rod-shaped radiation source providing radiation at, inter alia, a wavelength of 254 nm.

The radiation source is preferably a mercury-vapour lamp. The irradiation space is implemented at least on the side directed towards the radiation source, in a material which is transparent to radiation at the wavelength of 254 nm and preferably consists of quartz glass. The spirally guided flow produces secondary vortices, known as Dean vortices 200 (see FIG. 6), which generate efficient and effective cross-mixing of the liquid even in a laminar flow regime. In this way, all liquid components, while flowing through the module, irradiated in a layer close to the wall. In addition, this flow guidance brings about narrowing of the residence time.

Figure 4:
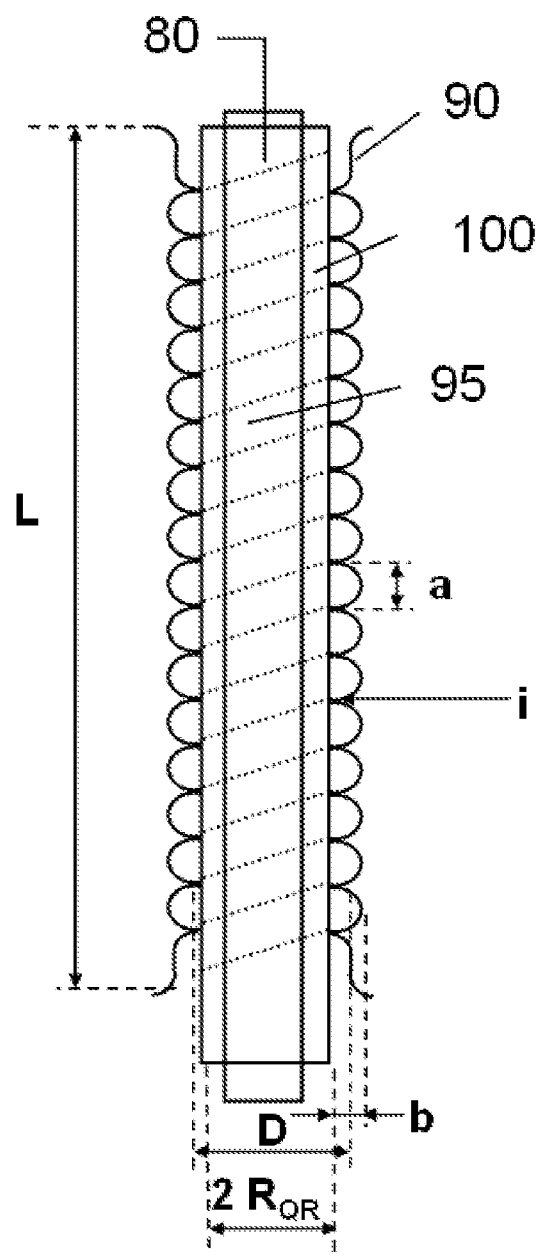
Figure 5:
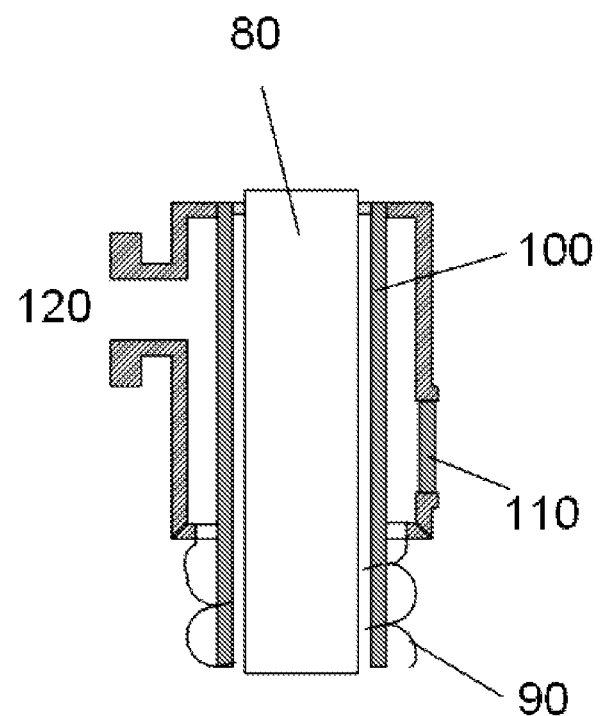
Figure 6:
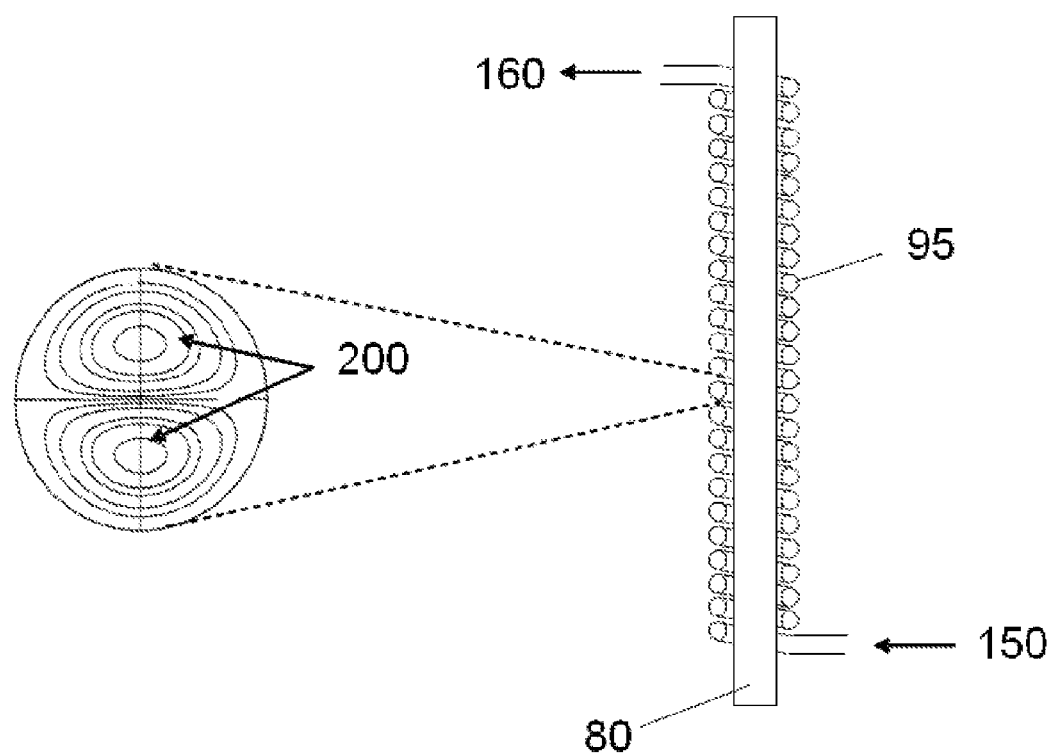

A preferred embodiment of a spiral module is shown in FIG. 4.

In this preferred embodiment, the spiral module comprises Teflon tubing 90 which has spiral notching and, as a result, forms a spiral. A quartz tube 100 is introduced in a force-fitted manner into said Teflon tubing. This structure separates the individual spirals 95 from one another and a spiral pipeline system is produced. A UV lamp 80 is introduced inside the quartz tube 100. This position makes it possible to maximally irradiate the solution flowing through the spirals on its entire way through the reactor.

Introduction of liquid is preferably effected via a lower inlet and thus permits bubble-free introduction of different solutions. At both the lower and the upper ends of the irradiation module, there is situated a reactor head (see FIG. 5) which is intended for the supply of liquid or the removal of liquid, respectively. A created opening 110 makes it possible to monitor the performance of the radiation source by means of a UV sensor.

In FIG. 4:
D=average diameter of a spiral
b=width of the semielliptic flow channel
L=length of the Teflon tubing
a=average height of a spiral
i=distance between two spirals
$R_{QR}$=one half of the external diameter of the quartz tube

EXAMPLE 3

Method for Treating the Medicinal-Leech Extract from Example 1 in the Device from Example 2

A medicinal-leech extract from the method according to example 1 was irradiated using a device according to example 2 having an irradiation module. This was initially charged with a volume of 230 ml of extract which had been admixed with a small amount (>10%) of virus stock solution (minute virus of mice). The optical density was 53.3. The extract was pumped through a 24 ml irradiation module at 10 l/h by a peristaltic pump, irradiated therein with UV light at 254 nm, and guided back to the initial charge (circulatory mode of operation). After 0, 10, 20 and 30 minutes, a sample was taken from the initial charge. This corresponds to an irradiation dose of 0, 97, 198 and 303 $J/m^2$, respectively. From each sample, standard assays were used to determine viral activity and the activity of the hirudin active substance in the extract.

Figure 7:
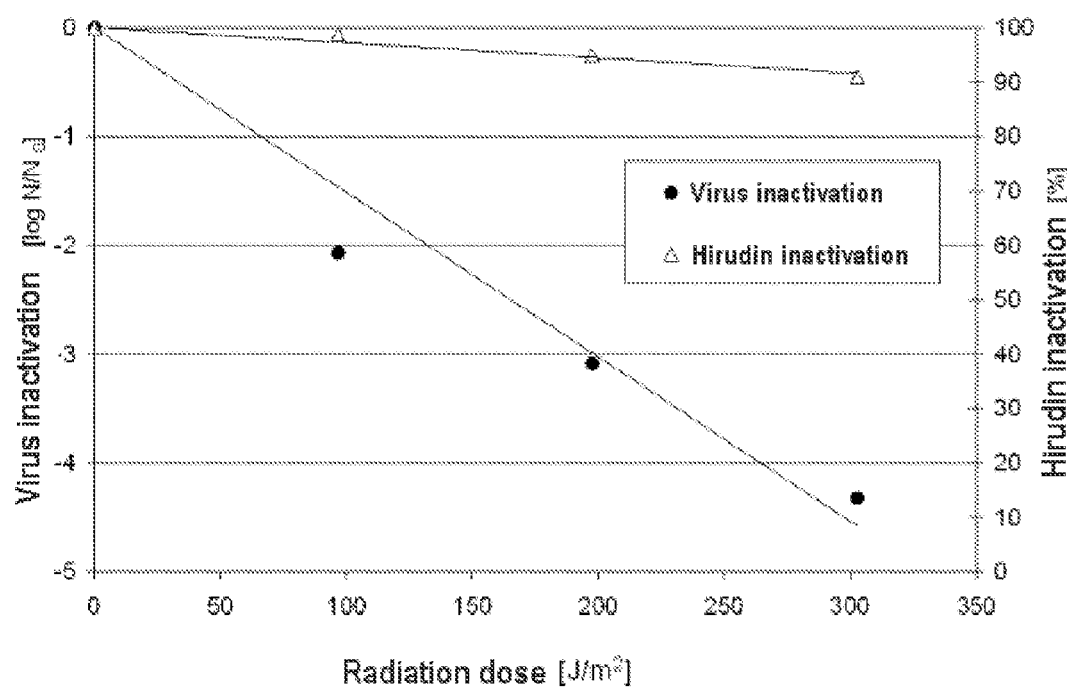

The results are shown in the graph in FIG. 7. FIG. 7 shows the inactivation of hirudin and of the added viruses as a function of irradiation dose. The result illustrates the clear virus-inactivating effect combined with limited damage to the active substance. However, since damage to the active substance is definitely present, it is necessary in the case of predefined minimum virus inactivation for very precise irradiation to be chosen in order to avoid unnecessary losses.

REFERENCE SYMBOLS 10 stirred vessel
15 medium (medicinal-leech extract)
20 spiral module
21 spiral module
30 conveyor (e.g. pump)
40 stirrer
50 cooling jacket
80 radiation source
90 Teflon tubing
95 spiral
100 quartz glass tube
110 closable opening for attaching a sensor
120 inlet/outlet
150 inlet
160 outlet

The invention claimed is:

1. Method for inactivating viruses and/or bacteria in a medicinal-leech extract, characterized in that the medicinal-leech extract is circulated between a stirred vessel and an irradiation device in which the medicinal-leech extract is irradiated using electromagnetic radiation.

2. Method according to claim 1, characterized in that irradiation is carried out using ultraviolet light in the range of 100 nm to 280 nm.

3. Method according to claim 1, characterized in that the medicinal-leech extract has an optical density in the range of up to 72.

4. Method according to claim 1, characterized in that the ratio of pump-circulated volumetric flow rate to total volume is in the range of 0.5 to 80 l/h.

5. Method according to claim 1, characterized in that the temperature of the medicinal-leech extract is maintained in the range of 2° C. to 25° C.

6. Method according to claim 1, characterized in that, before and/or after medicinal-leech extract irradiation, a transparent medium is conveyed through the system and the intensity of the radiation introduced into the medium or passed through the medium is measured.

7. Method according to claim 1, characterized in that the volume ratio between the stirred vessel and the irradiation device is in the range of 1 to 1000.

8. Method according to claim 1, characterized in that the irradiation device is formed by one or more preferably parallel-connected spiral modules, wherein a spiral module is a device providing at least one source of electromagnetic radiation and at least one channel winding helically around an axis.

9. Method according to claim 8, characterized in that the helically wound channel is arranged around a source of electromagnetic radiation.

10. Method according to claim 8, characterized in that the channel has a cross-sectional profile which is flattened on at least one side, and electromagnetic radiation is preferably introduced into the channel from this flattened side.

11. Method according to claim 8, characterized in that the cross-sectional profile of the channel is D-shaped, rhombus-shaped or rectangular.

12. Method according to claim 8, characterized in that the spiral module comprises a hollow cylinder onto which spiral tubing is mounted in a force-fitted or form-fitted manner and into which a source of electromagnetic radiation is introduced.

13. Method according to claim 8, characterized in that the spiral module is designed such that at least the irradiated components are used as disposable parts.

* * * * *